United States Patent
Smith (12)
(10) Patent No.: US 6,344,934 B1
(45) Date of Patent: Feb. 5, 2002

(54) HIGH DISPERSION, LASER PROTECTION LENS

(76) Inventor: David C. Smith, 44 Candlelight Dr., Glastonbury, CT (US) 06033

(*) Notice: Subject to any disclaimer, the term of this patent is extended or adjusted under 35 U.S.C. 154(b) by 0 days.

(21) Appl. No.: 09/617,449

(22) Filed: Jul. 17, 2000

(51) Int. Cl.$^7$ .......................... G02B 13/18; G02B 3/00; G02B 27/14; G02B 1/03; H01S 3/10
(52) U.S. Cl. ...................... 359/719; 359/642; 359/634; 359/241; 372/9
(58) Field of Search .................................. 359/719, 642, 359/722, 634, 241; 372/9, 99, 23

(56) References Cited

U.S. PATENT DOCUMENTS 5,831,769 A * 11/1998 Smith .......................... 359/634

* cited by examiner

Primary Examiner—Georgia Epps
Assistant Examiner—Michael A. Lucas
(74) Attorney, Agent, or Firm—M. P. Williams

(57) ABSTRACT

A lens includes a medium which absorbs laser radiation that may be harmful to the eye or other high gain optics raising its temperature and thereby changing its index of refraction, adjacent to a medium which does not absorb that radiation thereby providing a spatially fluctuating variation in total phase change, which causes interference and thermal blooming that disperses the radiation sufficiently to lower the intensity at the retinal spot (or optics to be protected) below that which would cause damage. Or, reflective surfaces on absorbing material have the same effect. Volumes which absorb or reflect laser radiation of a given band of frequencies are interspersed with volumes which do not absorb or reflect laser radiation of that given band of frequencies; the second volumes may be non-absorbing and non-reflecting, or may absorb laser radiation of a second band of frequencies. The fluctuation in absorption is small compared to total absorption, thereby to provide elements of radiation having different phases but sufficiently similar intensities. Two (or more) layers of absorbers provide protection from four (or more) bands of frequencies. Lead glass is used, for increased change in index as a function of temperature; and absorbing polycarbonate plastic is used for a lens substrate.

20 Claims, 5 Drawing Sheets

HIGH DISPERSION, LASER PROTECTION LENS

TECHNICAL FIELD

This invention relates to three dimensional, periodic absorption, phase change dispersing lenses having a near-unity intensity ratio for maximal laser dispersion.

BACKGROUND ART

In U.S. Pat. No. 5,831,769, a lens includes a medium which absorbs laser radiation that may be harmful to the eye or other high gain optics, raising its temperature and thereby changing its index of refraction in a pattern, which causes a phase change in the radiation passing therethrough. The medium may be periodically bounded by thermal sinks, thereby providing a periodic differential in temperature rise, may be provided in a length of absorption material which varies periodically or may have a density of absorption material which varies periodically, thereby to have a periodic absorption characteristic. The periodicity, which may be regular or random, provides a periodic variation in total phase change, which causes interference (thermal blooming) that disperses the radiation sufficiently to lower the intensity at the retinal spot, or other light-responsive surface, to a level below that which would cause damage. Eyeglasses with mutually perpendicular periodicity provide degraded vision of useful images while being protected from harmful radiation.

It has been determined that the foregoing laser protection lens is not as effective as possible, particularly per unit of axial thickness of the lens (parallel to the path of radiation to the eyes or instruments being protected thereby).

DISCLOSURE OF INVENTION

Objects of the invention include provision of laser protection lenses having the capability to reduce the intensity of received laser radiation at the focal plane (the retina or other light responsive surface) by an amount which is 10,000 times greater than the reduction of intensity to other radiation, particularly useful radiation, passing through the lens; laser protection lenses having laser dispersing characteristics many orders of magnitude greater than those heretofore attainable; laser protection lenses which are extremely effective, capable of protecting against incoming radiation of many tens of milliwatts per square centimeter while having a thickness of only several millimeters; and laser protection lenses capable of protecting against a plurality of distinct frequency bands of laser radiation.

According to the present invention, a lens for protecting optical systems having high optical gain, such as the human eye and optical instruments of high optical gain, induces thermal blooming of laser radiation passing therethrough by means of phase distortion created by a spatially-varying absorption or reflection characteristic.

In accordance with the invention, the disparity in absorption or reflection may be two dimensional (as in said patent) or may be three dimensional, as shown hereinafter.

According further to the present invention, the segments of varying absorption may take the form of a first section absorbing laser radiation of one or a plurality of frequency bands, and a second section having a plurality of groups of volumes, at least one group absorbing laser radiation of a first band of frequencies, and a second group of volumes not absorbing laser radiation of said first band; the second group may absorb no laser radiation, or may absorb laser radiation of a different frequency band. The second group of volumes may totally surround each volume in the first group, or the first and second volumes may be arranged in a matrix. In still further accord with the invention, there may be three different volumes, each absorbing laser radiation of a different band of frequencies; or, there may be two groups of volumes in one section adjacent the optical entry surface and two groups of volumes in another section adjacent said one section. According to the invention further, the groups of volumes may be arranged in a regular or irregular two-dimensional matrix.

In accordance with the invention, the second volumes, within the second section, may simply comprise strips disposed on an optical entry surface of the first section of a lens. In still further accordance with the invention, the strips may either be an absorption material, such as lead glass, or a reflecting material, such as a dielectric reflector formed in a suitable pattern by vapor deposition, by nanotechnology, or otherwise, directly on the optical entry surface of the first section.

An important aspect of the present invention is the potential to utilize vapor deposited reflecting elements, which may be quite thin, and have low weight. Such elements are easily made in virtually any pattern which can be achieved by low cost, conventional vapor deposition techniques.

According to the invention further, the various volumes for absorbing one or more bands of frequencies are formed of lead glass, so as to take advantage of a very high temperature coefficient of change of the index of refraction, thereby to achieve maximal phase difference and commensurate interference.

In accordance further with the invention, the absorption material may be submicron particles, or it may be a suitable dye.

Other objects, features and advantages of the present invention will become more apparent in the light of the following detailed description of exemplary embodiments thereof, as illustrated in the accompanying drawing.

MODES(S) FOR CARRYING OUT THE INVENTION

One principle of the invention is that the incoming radiation of a wavelength for which there is significant absorption in the absorption-portion of the lens will raise the temperature of the lens, thereby changing its index of refraction, and therefore altering the phase of the radiation as it exits the lens. If adjacent portions of the lens have absorption-portions of differing absorption, then the radiation exiting those different portions will be at different phases, and will therefore interfere, producing thermal blooming, which will disperse the radiation away from a focal point, thereby lowering the flux density of radiation at a point of interest, such as the retina or the light responsive portion of an optical equipment. The change in phase of radiation passing through the absorbing medium of the invention is given as $$\Delta\phi = \frac{2\pi\mu_T I t(1 - e^{-\alpha L})}{\lambda \rho C_p} \quad \text{(EQN. 1)}$$

where:

$\Delta\phi$=the change in phase due to absorption raising the temperature and thus changing the index of refraction $\mu_T$=the temperature coefficient of change of the index of refraction I=the intensity of the incoming radiation t=time duration of the laser radiation α=absorption per unit length for given wavelength L=length of absorbing segment λ=wavelength of incoming radiation ρ=density of the absorbing medium $C_{92}$=specific heat of the absorbing medium However, maximal dispersion or thermal blooming results from a maximal difference in phase between elements of radiation passing through the differently characterized segments of the lens at the far field (that is, near the retina or other focal plane which is to be protected). The phase difference will depend on the parameters of Equation 1 for each of the two classes of elements of radiation (those elements (a) passing through significant absorption or (b) or remaining after significant reflection, versus those elements passing through less absorption and without reflection) only if the intensity of each element of radiation is nearly the intensity of the other elements of radiation, as these elements of radiation leave the lens, radiating toward the focal plane. The actual difference in phase between elements of radiation having significant change in the index of refraction and elements of radiation not having that significant change at the retina (or other focal plane of interest) is ratioed by the square root of the ratio of their intensities, as follows:

$$\Delta\phi|_{I_A=I_C}=(I_A/I_C)^{1/2}\Delta\phi|_{I_A=I_C} \quad \text{(EQN. 2)}$$

where:

$\Delta\phi$=difference in phase of elements, at focal plane $I_A$=intensity of elements of radiation passing through highly absorbing or partly reflecting medium $I_c$=intensity of radiation passing through a more nearly clear or non-reflecting medium Thus, the closer the intensity of the elements of one phase is to the intensity of the elements of another phase, as the radiation leaves the lens, the more that the actual phase difference between the two elements of radiation at the focal plane will approach the potential phase difference at the focal plane. However, if the absorption for each element is made very large so that the difference in absorption between them will be small, then the useful light (ordinary ambient images) may be absorbed to such an extent that the lens becomes useless. As used herein, "absorb" and "absorption" do not imply complete absorption, but partial absorption determined by the parameters chosen in any implementation of the invention.

Figures 1, 2:
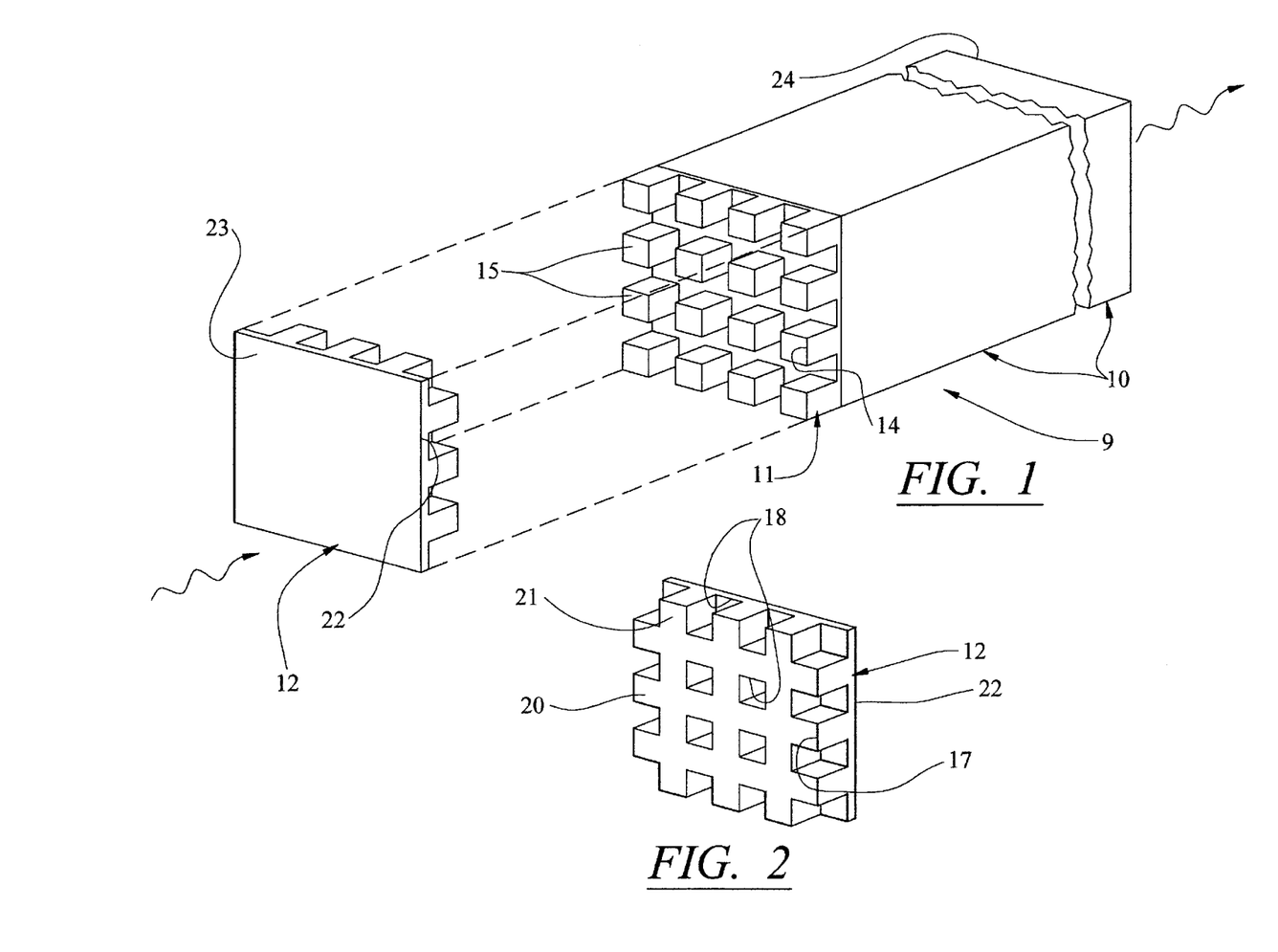
FIG. 1 is a exploded perspective view of an exemplary lens configuration in accordance with the present invention.
FIG. 2 is a perspective view of the lens configuration of FIG. 1 from a different view.
Figure 3:
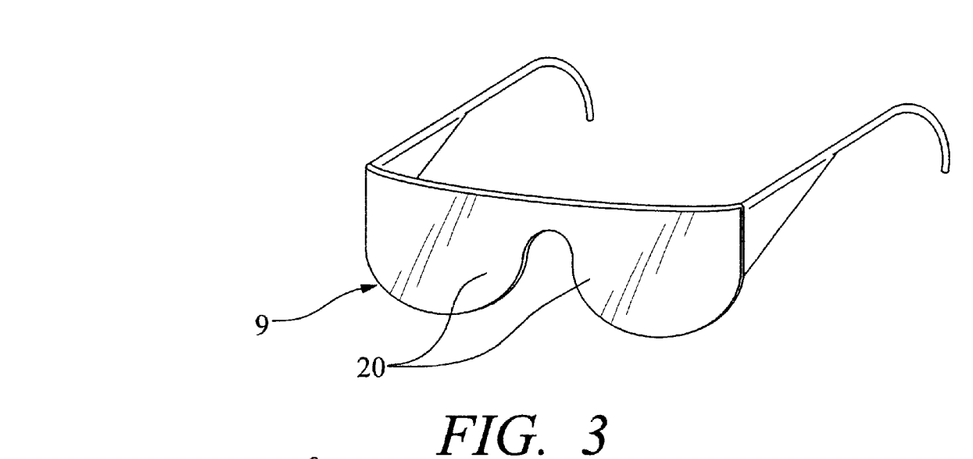
FIG. 3 is a perspective view of glasses which may incorporate the invention.
Figure 4:
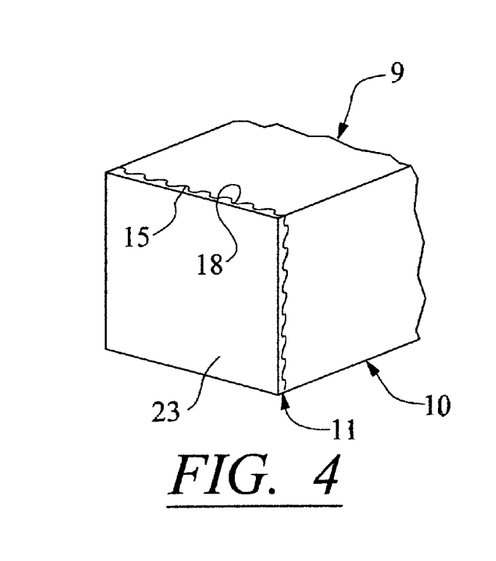
FIG. 4 is a partial, stylized illustration of wavy, three-dimensional irregularities.
Figure 5:
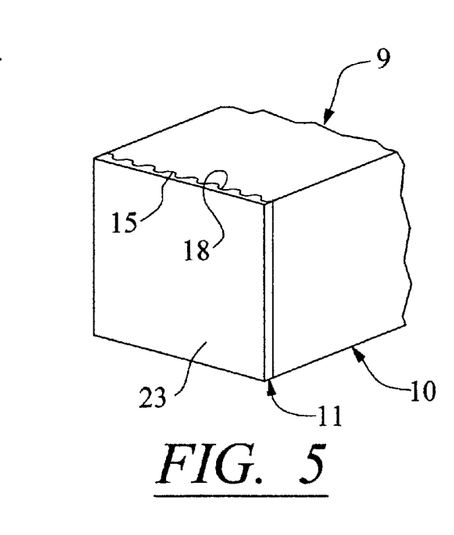
FIG. 5 is a partial, stylized illustration of wavy, two-dimensional irregularities.

Referring to FIGS. 1 and 2, a lens 9 according to the invention includes a first absorbing section 10, a second section including an absorbing portion 11 and a clear or non-absorbing portion 12. An internal surface 14 of the second absorbing portion 11 is provided with a plurality of waffle-iron-like protrusions or nobs 15, and a complementary internal surface 17 of the clear portion 12 includes a plurality of notches or holes 18 to receive the protrusions or nobs 15. The holes or notches 18 are formed by horizontal bars 20 which intermesh with vertical bars 21, both of which are supported by a thin section 22. In the embodiment of FIGS. 1 and 2, there are shown four rows and four columns of nobs and four rows and four columns of complementary notches or holes 18, for clarity of illustration. However, it is more likely that the number of discontinuities across the internal surfaces 14, 17 will be much greater, such as would be achieved with on the order of 10–20 rows and 10–20 columns. For ease of illustration, the embodiment of FIGS. 1 and 2 is shown as providing a square lens, having orthogonal discontinuities (nobs 15 and holes 18) therein. However, it is more likely in use that the overall shape of the lens 20 will be round or rounded, as shown in FIG. 3, rather than square, although the discontinuities may be orthogonal, as shown. The discontinuities may take other shapes, and may be more gradual and/or oriented on other axes, in regular or irregular patterns as illustrated in FIG. 4. In practicing the invention, the discontinuities or disparities in absorption may be three dimensional as shown in FIGS. 1, 2 and 4 herein, or may be two dimensional as shown in said patent and in FIG. 5 herein. The term "serpentine" is defined herein as describing the interface between absorbing and non-absorbing or less absorbing material, in any of the shapes described hereinbefore, and others. The lens substrate, that is, the portion 10 may comprise glass or plastic, such as allyldiglycolcarbonate (polycarbonate plastic), with particles of carbon soot, silica, or aluminum dispersed therein, all as described in the aforementioned patent, or with a suitable dye dispersed therein. Polycarbonate plastic is preferred, for safety of the eye or optics being protected. The dye may be chosen for a favorable absorption of wavelengths of radiation from which the high gain optical system (such as an eye or instrument) is to be protected. Different materials must be used for the portions 10, 11.

As an example only, the overall optical length of the lens from its optical entry surface 23 to its optical exit surface 24 may be on the order of 3 millimeters, and the optical length of the individual nobs 15 along the optical axis may be on the order of ½ millimeter. Increasing the length of the nobs 15 would increase the phase change for elements of radiation passing therethrough, and decrease the phase change for elements of radiation passing through the bars 20, 21, so that there would be a greater inherent phase difference between the elements of radiation as they leave the lens; however, the ratio in the far field, near the focal plane (such as the retina or other optically-responsive surface) would be commensurately reduced. Therefore, in accordance with the invention, the material of the nobs 15 must have a temperature coefficient of change of index of refraction that differs significantly from that of the section 10. The absorption is generally adjusted by the density or type of particles or dye in the material.

The intensity of radiation that passes through the nobs 15 is much less than the radiation that passes through the clear portion 12 (the bars 20 and 21). The interference which can occur between the diminished and undiminished waves is limited to the square root of the ratio of intensity. In turn, this means that there will be little interference between the two waves unless the phase change between the absorbed wave is very significant. Thus, the solution of one problem gives rise to another. In further accord with the present invention, the second absorbing portion 11, and therefore the nobs 15, is formed of a different material, such as lead glass, with a suitable dye or submicron particles dispersed therein, and the clear portion 12 is formed of lead glass (or other material) without any absorbing material therein. On the other hand, the portion 10 is preferably formed of polycarbonate plastic so that the portion 10 cannot shatter and therefore will not injure eyes or other objects to be protected by lenses of the invention. Low intensity radiation, insufficient to heat the portion 11, will have the same phase as it emerges either from the bars of the portion 12 or the nobs of the portion 11. However, when the intensity is great, the absorption in the portion 11 will cause a temperature rise to change the index of refraction and thereby induce a phase change within the portion 11 which is significantly different from that of the portion 12. Lead glass is preferably selected for the portions 11 and 12 because it has a temperature coefficient of change of the index of refraction, $\mu_T$, equal to on the order of $-2\times10^{-3}$, which is 20 times greater than that of polycarbonate (which is about $+10^{-4}$) and of the opposite sign. The portion 10 will have a suitable dye or submicron particles dispersed therein so as to be uniformly absorptive to all the radiation of wavelengths against which the eyes or optics are to be protected by the lens.

Figure 6:
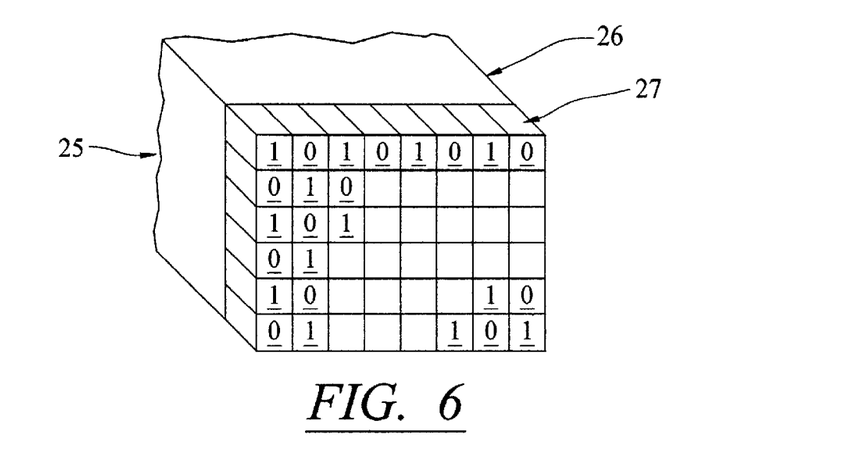
FIG. 6 is a stylized perspective view of an alternative form of the exemplary lens of FIG. 1.

Referring to FIG. 6, an alternative lens 25 includes a first section 26 that absorbs laser radiation, as described hereinbefore, of a desired band of frequencies. The lens 25 also has a second section 27 which is formed in the nature of an inlaid checkerboard, having volumes 0, 1 interspersed with each other in two dimensions. The volumes 1 absorb laser radiation of the desired band of frequencies to be protected, and the volumes 0 do not absorb laser radiation. Only some of the squares are numbered, for simplicity, but the remaining pattern repeats that which is shown. The lens of FIG. 6 differs from the lens of FIGS. 1 and 2 in that in FIG. 1, the absorbing nobs 15 are completely surrounded by the bars 20, 21 which do not absorb laser radiation, whereas in FIG. 6, the absorbing portions 1 are contiguous at the corners. However, it is not necessary that the first volumes 1 touch each other, it being possible to have the first volumes 1 smaller than the second volumes 0 so as to totally occlude each of the first volumes 1 with non-absorbing material. The second section should be adjacent the optical entry surface so as to maximize the thermal blooming effect.

Figure 7:
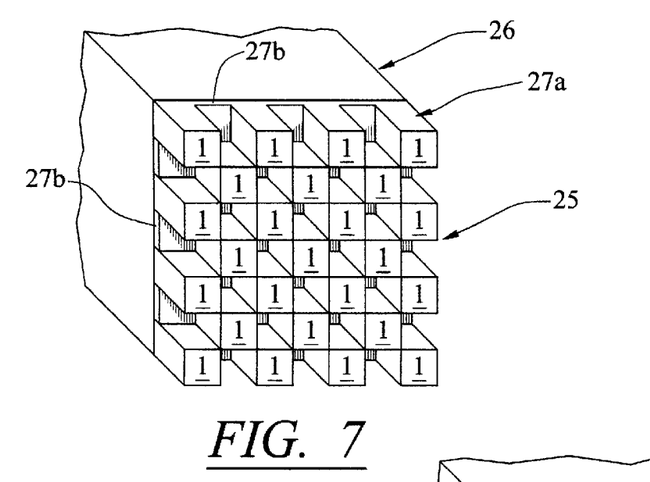
FIG. 7 is a perspective view of the lens of FIG. 6.

Referring to FIG. 7, the structure illustrated in FIG. 6 may be produced by providing a subsection 27a containing the volumes 1, and a like subsection (not shown), complimentary to the subsection 27a. In such a case, each of the volumes 1 will extend from a base portion 27b. The structure of FIG. 7 may be made by first forming a plurality of slots in a sufficiently thick piece of material, then cutting the material into rows, offsetting the rows so that the "teeth" of the subsections 27b will be in alternate positions as shown in FIG. 7, and joining all of the rows together. A similar subsection complimentary to subsection 27a could be made in the same fashion, except for providing that the outermost rows would have three "teeth", to intermesh with the four "teeth" of the outermost row shown in FIG. 7.

Figure 8:
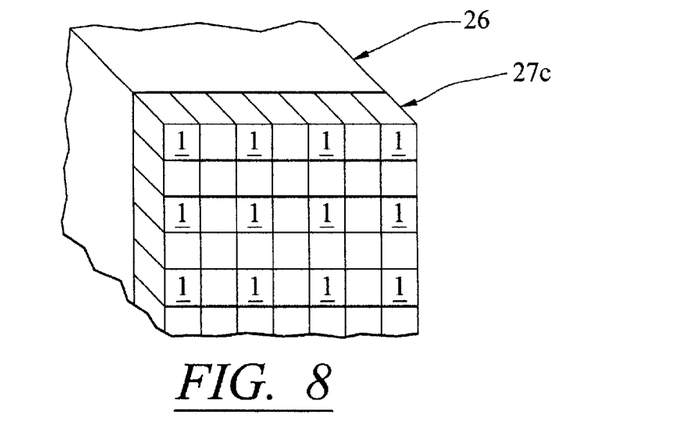
FIG. 8 is a stylized perspective view of the lens of FIGS. 1 and 2.

The embodiment of FIG. 1 could be made in a similar fashion as shown in FIG. 8, having a first section 26 that absorbs laser radiation of a first band of frequencies and a second section 27c having first portions 1 which are entirely surrounded by second portions 0 (the zero's being omitted in FIG. 8 for clarity). A second subsection (not shown) will have sufficient volumes 0 so as to form the horizontal bars 20 and vertical bars 21 illustrated in FIG. 2. Manufacture of the subsection 27c and the mating subsection would be as described with respect to FIG. 7.

Figure 9:
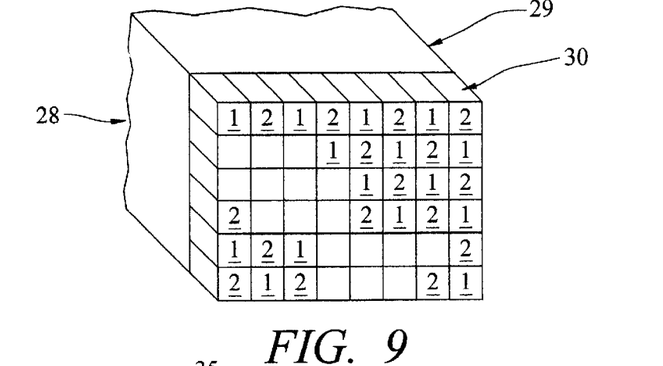
FIG. 9 is a perspective view of a lens for protection against two bands of laser radiation.

The lens 28 of FIG. 9 is similar to that of FIG. 6 except that the first section 29 absorbs laser radiation of a first band of frequencies and absorbs laser radiation of a second band of frequencies different from said first band of frequencies. A second section 30 has first volumes 1 which absorb laser radiation of said first band of frequencies and second volumes 2 which absorb laser radiation of said second band of frequencies. Thus, with no diminishment of the protection against the first band of frequencies, the embodiment of FIG. 9 will protect equally well against a second band of frequencies, also. The particular bands of frequencies absorbed depends on the particles or dye within the various sections and volumes of material.

Figure 10:
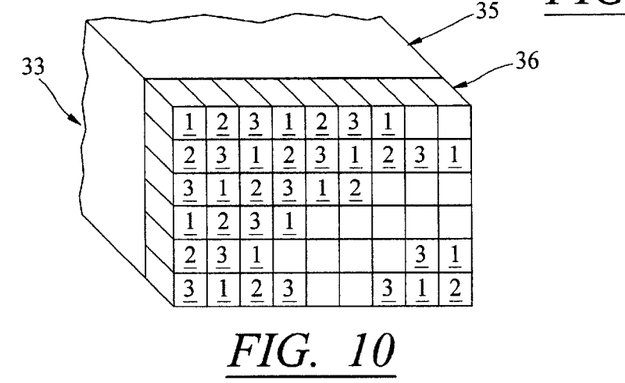
FIG. 10 is a perspective view for protecting against three bands of laser radiation.

In FIG. 10, a lens 33 includes a first section 35 that absorbs laser radiation of three different bands of frequencies, and a second section 36 having three groups of volumes 1–3, the volumes 1 absorbing laser radiation at a first band of frequencies, the volumes 2 absorbing laser radiation at a second band of frequencies, and the volumes 3 absorbing laser radiation at a third band of frequencies. In this case, all other parameters being equal, the dispersion of and therefore protection from, one of the bands of wavelengths is only two-thirds as great as it would be in the embodiments of FIGS. 6 and 7. However, that can be adjusted by other factors to restore it to the desired value.

Figure 11:
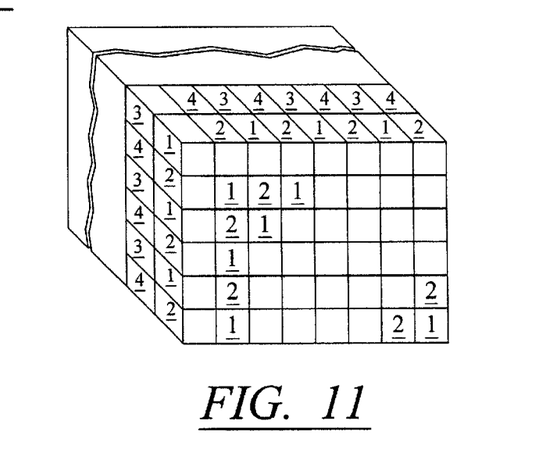
FIG. 11 is a perspective view of a lens having two volumes for absorbing selected laser radiation.

FIG. 11 illustrates an embodiment in which four different bands of frequencies can be protected against without diminishing the protection of any of the bands of frequencies. This is accomplished simply by having volumes 3, 4 adjacent to volumes 1, 2. One additional set of volumes or more may be added: however, if the first section remains full length so as to maintain a near-unity ratio at the optical target, the total attenuation will increase to reduce normal vision; if the first section length is reduced to compensate for the fourth or more sections, the ratio will become smaller, thereby reducing the thermal blooming dispersion effect.

The embodiments of FIGS. 6 and 9–11 are shown as being rectangular, with equally sized volumes 0–3. FIGS. 6, 9 and 10 indicate that, unlike FIG. 1, the number of absorbing volumes in the horizontal direction can differ from the number of like volumes in the vertical direction; FIGS. 1 and 2 being four by four, FIGS. 6 and 9 being three by four (having a three by six grid), and FIGS. 10 and 11 being two by three (having a six by nine grid). Of course, lenses of the invention may be designed to protect against four or more wavelengths in accordance with the teachings hereinbefore. The volumes illustrated in FIGS. 6 and 9–11 need not be regular, the intersections need not be straight, and various designs may be utilized, as described hereinbefore.

Figure 12:
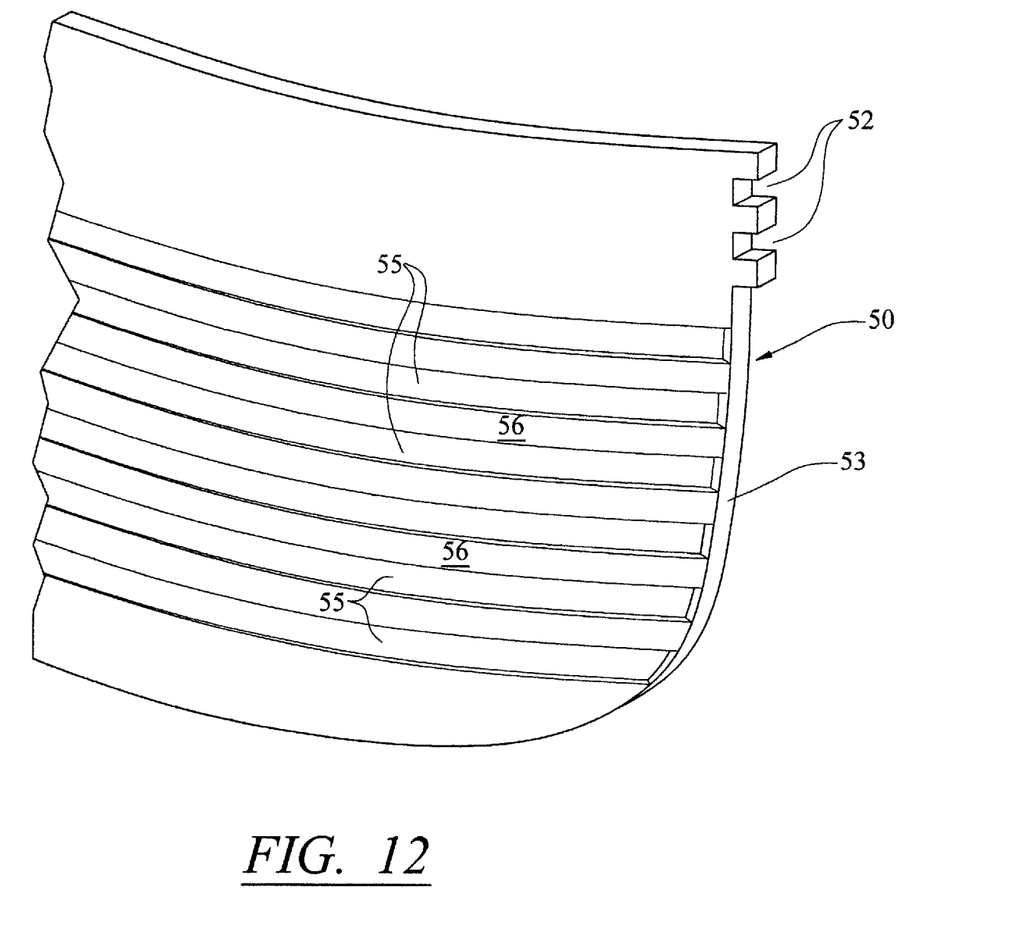
FIG. 12 is a perspective view of a lens having strips disposed on an optical entry surface.

Referring to FIG. 12, a lens 50 (only a fragment being shown) may have a hinge portion 52 formed in a substrate 53, which comprises a first section and may preferably be polycarbonate glass with either micron size particles or a suitable dye disposed therein so as to provide uniform absorption of a desired band of frequencies. On the substrate 53, a plurality of strips 55 comprise first volumes of a second section. The strips 55 may, in some cases, be lead glass having suitable submicron particles or dye disposed therein so as to absorb laser radiation of the same band of frequencies as is absorbed by the first section 53. On the other hand, strips 55 may be reflective material, such as vapor deposited dielectric reflector. Utilizing a reflector as the first group of volumes (within the second section) results in a much lower intensity of radiation entering the optical input surface of the first section 53 from behind the strips 55 than the intensity of radiation entering the first section 53 through any of the interstices 56 between the strips 55. Therefore, when high intensity laser radiation impinges on the lens 50, the intensity of radiation, being of a much lower level behind the strips 55, will not heat the lens as much as will the more intense radiation passing through the interstices 56. Therefore, there will be a much greater phase change induced in the radiation passing through the interstices 56 than there will be through the reflective strips 55. This will produce the same sort of interference, thermal blooming and dispersion as is described hereinbefore. The thickness and width of the strips 55 as well of the interstices 56 have been greatly exaggerated in FIG. 12 for clarity.

The invention may be practiced utilizing reflective surface in a variety of shapes, in addition to the strips illustrated in FIG. 12. As an example, in FIG. 6, the volumes marked "1" may be reflectors on the optical entry surface of the first section 26, whereas the volumes marked "0" would simply be the interstices between the reflectors. Any other suitable shapes may be chosen as desired.

Two different reflective materials may be used, one reflecting one band of laser frequencies and another reflecting another band of laser frequencies. In such case, operation is essentially the same as that described with respect to FIG. 9 hereinbefore.

Preliminary calculations have shown that an optimum configuration for a reflective embodiment of the present invention will have 50% of the optical entry surface covered by reflective surfaces, the remaining 50% of the optical entry surface consisting of interstices between the reflective surfaces. In such a case, reflective surfaces which have 66% reflectivity will provide a maximal amount of phased differential as the radiation passes through the lens.

The aforementioned patent is incorporated herein by reference.

Thus, although the invention has been shown and described with respect to exemplary embodiments thereof, it should be understood by those skilled in the art that the foregoing and various other changes, omissions and additions may be made therein and thereto, without departing from the spirit and scope of the invention.

I claim:

1. A lens for protecting optics having optical gain and an optical axis from laser radiation, said lens having a lens optical axis which is coaligned with the optical axis of said optics and having an optical entry surface, comprising:
   a first section disposed around said lens optical axis for absorbing laser radiation and having a first temperature coefficient of change of index of refraction; and
   a second section disposed adjacent to said first section and to said optical entry surface along said lens optical axis and having at least one group of volumes, said one group of volumes either (a) having a second temperature coefficient of change of index of refraction which is significantly different from said first temperature coefficient of change of index of refraction and absorbing laser radiation of a selected band of frequencies, or (b) reflecting laser radiation of a selected band of frequencies, there being interstices between the volumes of said one group, said interstices not absorbing or reflecting, respectively, any significant amount of laser radiation of said selected band of frequencies; and
   said first section absorbing laser radiation of said selected band of frequencies.

2. A lens according to claim 1 wherein:
said one group of volumes is arranged in a two-dimensional matrix.

3. A lens according to claim 2 wherein:
said matrix is irregular.

4. A lens according to claim 2 wherein:
said matrix is regular.

5. A lens according to claim 1 wherein:
said interstices do not absorb or reflect, respectively, any significant amount of laser radiation.

6. A lens according to claim 1 wherein:
said one group of volumes absorbs laser radiation of said selected band of frequencies;
said interstices contain a second group of volumes which absorb laser radiation of a second band of frequencies different from said selected band of frequencies; and
said first section absorbs laser radiation of said selected band of frequencies and of said second band of frequencies.

7. A lens according to claim 1 wherein:
there are three groups of volumes in said second section;
said one group of volumes absorbs laser radiation of said selected band of frequencies;
each of said three groups absorbs laser radiation of a band of frequencies which differs from the band of frequencies absorbed by the other two of said groups; and
said first section absorbing laser radiation of any band of frequencies as is absorbed by the volumes of said second section.

8. A lens according to claim 1 wherein:
said one group of volumes absorbs laser radiation of said selected band of frequencies; and
said first volumes comprise lead glass with either (1) micron size particles suspended therein or (2) a dye disposed therein.

9. A lens according to claim 8 wherein:
said first section comprises polycarbonate plastic with either (1) micron size particles suspended therein or (2) a dye disposed therein.

10. A lens according to claim 1 wherein:
said first section comprises polycarbonate plastic with either (1) micron size particles suspended therein or (2) a dye disposed therein.

11. A lens according to claim 1 wherein said first volumes comprise reflectors.

12. A lens according to claim 11 wherein said first volumes comprise dielectric reflectors.

13. A lens according to claim 1 wherein:
said first section has an optical entry surface; and
said first volumes of said second section comprises strips disposed on the optical entry surface of said first section.

14. A lens according to claim 13 wherein:
said first volumes comprise absorption material.

15. A lens according to claim 14 wherein:
said first volumes comprise a medium having (a) submicron particles or (b) a dye dispersed therein having a cross section of absorption for laser radiation of said selected band of frequencies; and the interstices between said first volumes comprise strips of said medium without submicron particles or dye dispersed therein.

16. A lens according to claim 15 wherein said medium comprises lead glass.

17. A lens according to claim 13 wherein said strips comprise reflectors.

18. A lens according to claim 17 wherein said strips comprise dielectric reflectors.

19. A lens according to claim 13 wherein said first section comprises a medium having (a) submicron particles or (b) a dye dispersed therein having a cross section of absorption for laser radiation of said selected band of frequencies.

20. A lens according to claim 19 wherein said medium comprises polycarbonate plastic.

* * * * *